US007786089B2

(12) United States Patent
Kandimalla et al.

(10) Patent No.: US 7,786,089 B2
(45) Date of Patent: Aug. 31, 2010

(54) IMMUNOSTIMULATORY ACTIVITY OF IMMUNE MODULATORY OLIGONUCLEOTIDES (IMO™) CONTAINING DIFFERENT LENGTHS OF PALINDROMIC SEGMENTS

(75) Inventors: Ekambar R. Kandimalla, Southboro, MA (US); Mallikarjuna Reddy Putta, Burlington, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 632 days.

(21) Appl. No.: 11/641,551

(22) Filed: Dec. 19, 2006

(65) Prior Publication Data
US 2007/0219153 A1  Sep. 20, 2007

Related U.S. Application Data

(60) Provisional application No. 60/752,336, filed on Dec. 20, 2005.

(51) Int. Cl.
*A61K 31/70* (2006.01)
*C12N 5/02* (2006.01)
*C07H 19/00* (2006.01)
*C07H 21/02* (2006.01)

(52) U.S. Cl. .................. 514/44 R; 435/325; 435/375; 536/22.1; 536/23.1; 536/24.5

(58) Field of Classification Search ........................ None
See application file for complete search history.

(56) References Cited

U.S. PATENT DOCUMENTS

| 5,366,878 | A | 11/1994 | Pederson et al. |
| 5,635,377 | A | 6/1997 | Pederson et al. |
| 5,652,355 | A | 7/1997 | Metelev et al. |
| 5,994,361 | A | 11/1999 | Penney et al. |
| 6,143,881 | A | 11/2000 | Metelev et al. |
| 6,346,614 | B1 | 2/2002 | Metelev et al. |

| 2003/0175731 | A1 | 9/2003 | Fearon et al. |
| 2004/0097719 | A1 | 5/2004 | Agrawal et al. |

OTHER PUBLICATIONS

Kuramoto et al., "Oligonucleotide Sequences Required for Natural Killer Cell Activation", Jpn. J. Cancer Res., 83:1128-1131 (1992).
Tokunaga et al., Investigations on nonhuman Systems, J. Natl. Cancer Inst., 72:955-962 (1984).
Pisetsky et al., "Stimulation of In Vitro Proliferation of Murine Lymphocytes by Synthetic Oligodeoxynucleotides", Mol. Biol. Rep., 18:217-221 (1993).
Krieg et al., "CpG Motifs in Bacterial DNA Trigger Direct B-Cell Activation", Nature, 374:546-549 (1995).
Sato et al., "Immunostimulatory DNA Sequences Necessary for Effective Intradermal Gene Immunization", Science, 273(5273):352-355(1996).
Krieg et al., "CpG Motifs in Bacterial DNA and Their Immune Effects", Annul. Rev. Immunol. 20:709-760 (2002).
Dalpke et al., "Immunopharmacology of CpG DNA", Biol. Chem., 383:1491-1500 (2002).
Kandimalla et al., "Towards Optimal Design of Second-Generation Immunomodulatory Oligonucleotides", Curr. Opin. Mol. Ther. 4(2):122-129 (2002).
Kandimalla et al., "Immunomers—Novel 3'-3'-Linked CpG Oligodeoxyribonucleotides as potent Immunomodulatory Agents", Nuc. Acids Res., 30(20):4460-4469 (2002).
Kandimalla et al., "Secondary Structures in CpG Oligonucleotides Affect Immunostimulatory Activity", Biocehm. Biophys. Res. Commun., 306:948-953 (2003).
Liang et al., "DNA Sequence Preferences of GAL4 and PPR1: How a Subset of $Zn_2Cys_6$ Binuclear Cluster Proteins Recognizes DNA", Mol. Cell. Biol., 16(7):3773-3780 (1996).
Nguyen et al., "Transcriptional Regulation of the Antioxidant Response Element", J. Biol. Chem., 275(20):15466-15473 (2000).
Remington's Pharm. Sci., 19th Edition, ed. A. Gennaro, Mack Publishing Co., Easton, PA 1990.
Burgstaller et al., "Aptamers and Apazymes: Accelerating Small Molecule Drug Discovery", Curr. Opin. Drug. Discov. Devel., 5(5):690-700 (2002).

*Primary Examiner*—Janet L Epps-Smith
(74) *Attorney, Agent, or Firm*—Wayne A. Keown; Preti Flaherty

(57) ABSTRACT

The invention provides a palindromic immune modulatory nucleic acid. The invention also provides methods for generating, enhancing and modifying the immune response caused by palindromic immune modulatory compounds used for immunotherapy applications.

8 Claims, 9 Drawing Sheets

Linkers for linear synthesis

SEQUENCE LISTING

<160> NUMBER OF SEQ ID NOS: 18

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

```
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 1
tcntcnttct c                                                              11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 2
tcntcnttct c                                                              11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 3
tcntcnttct c                                                              11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 4
tcntcnttct c                                                              11

<210> SEQ ID NO 5
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 5
tcntcnttag a                                                                11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG

<400> SEQUENCE: 6
tcnaacnttc n                                                                11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 7
tcntcnttct g                                                                11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 8
```

```
tctgacnttc t                                                    11
```

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
acacaccaac t                                                    11
```

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 10

```
tcntcnttc                                                        9
```

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG

<400> SEQUENCE: 11

```
tcntcnttc                                                        9
```

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG

<400> SEQUENCE: 12
tcnaacnttc n                                                       11

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 7-deaza-dG
<220> FEATURE:
<221> NAME/KEY: modified_base
<222> LOCATION: (9)
<223> OTHER INFORMATION: 7-deaza-dG
<220> FEATURE:
<221> NAME/KEY: modified_base
<222> LOCATION: (13)
<223> OTHER INFORMATION: 7-deaza-dG

<400> SEQUENCE: 13
tctcnaacnt tcnag                                                   15

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG
<220> FEATURE:
<221> NAME/KEY: modified_base
<222> LOCATION: (15)
<223> OTHER INFORMATION: 7-deaza-dG

<400> SEQUENCE: 14
tctctcnaac nttcnagag                                               19

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cggcgcgccg                                                         10

<210> SEQ ID NO 16
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:

```
<221> NAME/KEY: modified_base
<222> LOCATION: (6)
<223> OTHER INFORMATION: 7-deaza-dG

<400> SEQUENCE: 16 tcntcnt                                                                    7

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG

<400> SEQUENCE: 17
tcnaacnttc n                                                              11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (11)
<223> OTHER INFORMATION: 7-deaza-dG

<400> SEQUENCE: 18
tcnaacnttc n                                                              11
```

IMMUNOSTIMULATORY ACTIVITY OF IMMUNE MODULATORY OLIGONUCLEOTIDES (IMO™) CONTAINING DIFFERENT LENGTHS OF PALINDROMIC SEGMENTS

RELATED APPLICATIONS

This application claims the benefit of U.S. Provisional Application Ser. No. 60/752,336, filed Dec. 20, 2005. The entire teachings of the above-referenced Application are incorporated herein by reference.

BACKGROUND OF THE INVENTION

1. Field of the Invention

The invention relates to immune stimulation by chemically modified palindromic oligonucleotide analogs.

2. Summary of the Related Art

Kuramoto et al., Jpn. J. Cancer Res. 83:1128-1131 (1992) teaches that phosphodiester oligonucleotides containing a palindrome that includes a CpG dinucleotide can induce interferon-alpha and interferon-gamma synthesis and enhance natural killer activity. Tokunaga et al., J. Natl. Cancer Inst. 72 (1984) 955-96. Pisetsky et al.; Reich et al., Mol. Biol. Rep. 18 (1993) 217-221; Krieg et al., Yi e al., Nature 374 (1995) 546-549 and Sato et al., Science 273 (1996) 352-354 teach that bacterial DNA, synthetic oligodeoxynucleotides, and DNA vaccines containing unmethylated CpG-dinucleotides in specific sequence contexts (CpG DNA) activate the vertebrate immune system.

Toll-like receptors (TLRs) function as sensors of infection and induce the activation of innate and adaptive immune responses. TLRs recognize a wide variety of ligands, called pathogen-associated molecular patterns (PAMPs). Upon recognizing conserved pathogen-associated molecular products, TLRs activate host defense responses through their intracellular signaling domain, the Toll/interleukin-1 receptor (TIR) domain, and the downstream adaptor protein MyD88. Dendritic cells and macrophages normally respond to Toll-like receptor (TLR) ligands and cytokines (for example, interleukin-1$^\beta$; IL-6 and tumor necrosis factor, TNF), which they also produce; natural killer (NK) cells and T cells are also involved in the pro-inflammatory circuit. After TLR stimulation by bacterial compounds, innate immune cells release a range of cytokines and chemokines. Some examples of TLR ligands include, but are not limited to, lipoproteins; peptidoglycan, zymosan (TLR2), double-stranded RNA, polyI:polyC (TLR3), lipopolysaccharide, heat shock proteins, taxol (TLR4), flagellin (TLR5), and imidazoquinolines-R848, resiquimod, imiquimod; ssRNA (TLR7/8), beta-lymphocytes (TLR10), and profilium like molecules and uropathogenic E. coli (TLR11).

Krieg et al., Annu. Rev. Immunol. 20 (2002) 709-760; Dalpke et al., Biol. Chem. 383 (2002) 1491-1500 and Kandimalla et al., Curr. Opin. Mol. Ther. 4 (2002) 122-129 teach that CpG DNAs induce innate immune cells to produce Th1 cytokines that promote cytotoxic T lymphocyte (CTL) responses and production of immunoglobulins by B cells. The immune stimulatory properties of CpG DNAs have allowed their use as therapeutic agents for a broad spectrum of disease indications including cancers, viral and bacterial infections, inflammatory disorders and as adjuvant in immunotherapy.

In addition to chemical modifications, a number of structural modifications influence the activity of CpG DNAs. Kandimalla et al., Nucleic Acids Res. 30 (2002) 4460-4469 teaches that CpG DNAs that contained two freely accessible 5'-ends through a 3'-3'-linkage had greater activity than did conventional CpG DNAs containing multiple copies of CpG motifs and a single 5'-end.

Kandimalla et al., Biochem. Biophys. Res. Commun. 306 (2003) 948-953 teaches that the presence of a secondary structure in CpG DNAs significantly affected their activity depending on the position and nature of the secondary structure, that the presence of a hairpin structure at the 5'-end abrogated stimulatory activity, and that the same structure at the 3'-end had an insignificant effect on stimulatory activity but caused lower IL-6 secretion and contributed to higher stability against nucleases.

One skilled in the art would recognize that incorporating a palindrome into an immune stimulatory oligonucleotide could result in a molecule with undesired protein binding characteristics. For example, Liang et al., Mol. Cell. Biol. 16(7): 3773-3780 (1996) show that for GAL4, the palindromic CGG triplets at the ends of the 17-bp DNA recognition site are essential for tight binding and that PPR1, a relative of GAL4, also recognizes palindromic CGG triplets at the ends of its 12-bp DNA recognition sequence. In addition, Nguyen et al., J Biol. Chem. 275:15466-15473 (2000) show that a palindromic sequence within the hNQO$_1$ ARE/EpRE DNA recognition motif is necessary for binding of Nrf2/MafK heterodimer and cannot be competed by the ARE/EpRE sequence of rGSTA2, which does not contain the palindromic sequence. This binding of proteins to oligonucleotides is recognized as a limiting factor in using those oligonucleotides for immune stimulation compositions. However, incorporating a chemically modified palindrome into an immune modulatory oligonucleotide and/or 3'-3' linking of chemically modified palindromic immune modulatory oligonucleotides could produce a molecule with the desired immune modulatory characteristics without the limitations of a natural, linear palindrome.

Thus, there remains a need to develop palindrome-containing compounds that modulate an immune response through TLRs but that are not plagued with the problems of linear oligonucleotides containing unmodified palindromic segments.

BRIEF SUMMARY OF THE INVENTION

In a first aspect the invention provides an immune modulatory oligonucleotide having a structure selected from the group of 5'-TCG$_1$TCG$_1$TTCTC-Y-G$_1$ CTTG$_1$CAAG$_1$CT-5' (SEQ ID NOS 1 and 12), 5'-TCG$_1$TCG$_1$TTCTC-Y-GAG$_1$CTTG$_1$CAAG$_1$CTCT-5' (SEQ ID NOS 2 and 13), 5'-TCG$_1$TCG$_1$TTCTC-Y-GAGAG$_1$CTTG$_1$CAAG$_1$CTCTCT-5' (SEQ ID NOS 3 and 14), 5'-TCG$_1$TCG$_1$TTCTC-Y-GCCGCGCGGC-5' (SEQ ID NOS 4 and 15), 5'-TCG$_1$TCG$_1$TTAGA-Y-TG$_1$CTG$_1$CT-5' (SEQ ID NOS 5 and 16), 5 and 5'-TCG$_1$TCG$_1$TTC-Y-G$_1$CTTG$_1$CAAG$_1$CT-5 (SEQ ID NOS 10 and 17); wherein X is a glycerol linker, Y is C3-linker and G$_1$ is 7-deazaguanosine.

In a second aspect the invention provides pharmaceutical compositions. These compositions comprise any of the compositions disclosed in the invention and a pharmaceutically acceptable carrier.

In a third aspect the invention provides a method for generating an immune response in a vertebrate. This method comprises administering to the vertebrate any one of the compositions, alone or in combination, disclosed in the first and second aspects of the invention. The compositions disclosed herein can be administered through any suitable route of administration including, but not limited to, parenteral, oral, sublingual, transdermal, topical, mucosal, inhalation, intranasal, aerosol, intraocular, intratracheal, intrarectal, vaginal, gene gun, dermal patch, eye drop and mouthwash.

In a fifth aspect the invention provides a method for therapeutically treating a vertebrate having cancer, an autoimmune disorder, airway inflammation, inflammatory disorders, skin disorders, allergy, asthma or a disease caused by a pathogen. This method comprises administering to the vertebrate any one of the compositions, alone or in combination, disclosed in the first and second aspects of the invention in a pharmacologically effective amount. The compositions disclosed herein can be administered through any suitable route of administration including, but not limited to, parenteral, oral, sublingual, transdermal, topical, mucosal, inhalation, intranasal, aerosol, intraocular, intratracheal, intrarectal, vaginal, gene gun, dermal patch, eye drop, ear drop and mouthwash.

In a sixth aspect the invention provides a method for preventing cancer, an autoimmune disorder, airway inflammation, inflammatory disorders, skin disorders, allergy, asthma or a disease caused by a pathogen in a vertebrate. This method comprises administering to the vertebrate any one of the compositions, alone or in combination, disclosed in the first and second aspects of the invention in a pharmacologically effective amount. The compositions disclosed herein can be administered through any suitable route of administration including, but not limited to, parenteral, oral, sublingual, transdermal, topical, mucosal, inhalation, intranasal, aerosol, intraocular, intratracheal, intrarectal, vaginal, gene gun, dermal patch, eye drop, ear drop and mouthwash.

DETAILED DESCRIPTION OF THE PREFERRED EMBODIMENTS

Figure 1:
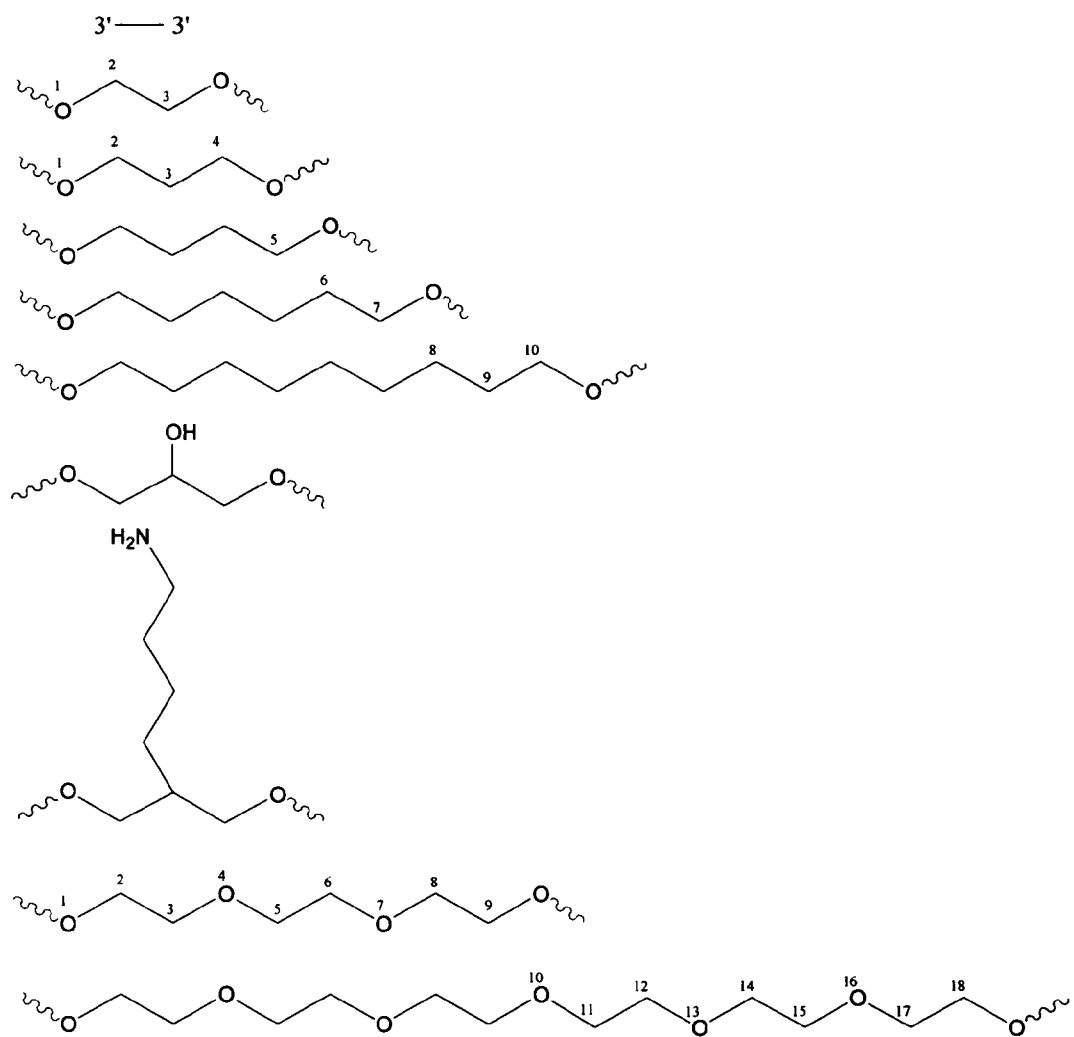
FIG. 1 depicts a group of representative small molecule linkers suitable for linear synthesis of palindromic immune modulatory oligonucleotides of the invention.

The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention relates to the therapeutic use of palindromic oligonucleotides as immune modulatory agents for immunotherapy applications. The invention also provides methods for generating, enhancing and modifying the immune response caused by palindromic immune modulatory compounds used for immunotherapy applications such as, but not limited to, treatment and/or prevention of cancer, autoimmune disorders, asthma, respiratory allergies, food allergies, and bacteria, parasitic, and viral infections in adult and pediatric human and veterinary applications. Allergic asthma is a certain embodied condition for treatment by the present methods and compounds. Thus, the invention further provides compounds having optimal levels of palindromic immune modulatory effect for immunotherapy and methods for making and using such compounds. In addition, palindromic immune modulatory oligonucleotides of the invention are useful as adjuvants in combination with DNA vaccines, antibodies, antigens, allergens, chemotherapeutic agents, and antisense oligonucleotides.

The term "palindromic immune modulatory oligonucleotide" generally refers to a palindromic immune modulatory oligonucleotide containing a palindromic sequence having a CG dinucleotide within the palindromic sequence. In certain embodiments, the cytosine and/or guanosine of the CG dinucleotide within the palindomic sequence is modified, provided that the palindromic immune modulatory oligonucleotide would not be suspected of being subject to undesired protein binding as compared to a linear, unmodified palindromic oligonucleotide while still maintaining, and even customizing, the immune response. The palindromic immune modulatory oligonucleotide may contain modified oligonucleotides and oligonucleosides, or combinations thereof. The palindromic immune modulatory oligonucleotide can be linear or branched, with nucleic acids being polymers of nucleosides linked through, for example, phosphodiester, phosphorothioate, or alternate linkages. A palindromic immune modulatory oligonucleotide may consist of a purine (adenine (A), inosine (I) or guanine (G) or derivatives thereof) or pyrimidine (cytosine (C), uracil (U) or thymine (T), or derivatives thereof) base covalently attached to a ribose sugar residue, or a derivative thereof.

In a first aspect, the invention provides palindromic immune modulatory oligonucleotide compound according to IMO™ Nos 1, 2, 3, 4, 10, or 11. The present inventors have discovered that modification of the cytosine and/or guanosine of the CG dinucleotide within the palindomic sequence and 3'-3' linking of linear palindromic immune modulatory oligonucleotides affects the immune modulatory capabilities of the palindromic sequence. Without wishing to be bound to any particular theory, the present inventors expect that this modification alters the palindromic portion such that the palindromic immune modulatory oligonucleotide's activity is not altered by undesired protein binding as compared to an unmodified palindromic oligonucleotide while still maintaining, and even customizing, the immune response.

This aspect the invention provides palindromic immune modulatory nucleic acid having an nucleic acid sequence containing at least one dinucleotide selected from CpG*, C*pG and C*pG*, wherein C is cytosine or 2'-deoxycytosine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

In some embodiments, the palindromic immune modulatory oligonucleotide is from about 2 to about 50 nucleotides in length. In certain embodiments the palindromic immune modulatory oligonucleotide is from about 11 to about 30 nucleotides in length. In some embodiments, the palindromic immune modulatory oligonucleotides are from about 3 to about 35 nucleoside residues, or from about 4 to about 30 nucleoside residues, or from about 7 to about 19 nucleoside residues. In some embodiments, the palindromic immune modulatory oligonucleotides have from about 5 to about 18, or from about 7 to about 11, nucleoside residues. As used herein, the term "about" implies that the exact number is not critical. Thus, the number of nucleoside residues in the oligonucleotides is not critical, and palindromic immune modulatory oligonucleotides having one or two fewer nucleoside residues, or from one to several additional nucleoside residues are contemplated as equivalents of each of the embodiments described above. In some embodiments, one or more of the palindromic immune modulatory oligonucleotides have 11 nucleotides.

In additional embodiments of this aspect, the invention provides an immune modulatory oligonucleotide comprising at least two immune modulatory oligonucleotides linked through their 3'-ends or internucleoside linkages or a functionalized nucleobase or sugar by a non-nucleotide linker, wherein the sequence of at least one of the immune modulatory oligonucleotides contains a palindromic immune modulatory oligonucleotide. In embodiments according to this aspect of the invention at least one of the palindromic immune modulatory oligonucleotides contains at least one dinucleotide selected from CpG*, C*pG and C*pG*, wherein C is cytosine or 2'-deoxycytosine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

The term "non-nucleotide linker" generally refers to any linkage or moiety that can link or be linked to the oligonucleotides other than through a phosphorous-containing linkage. Preferably such linker is from about 2 angstroms to about 200 angstroms in length. The term "nucleotide linkage" generally refers to a direct 3'-5' linkage that directly connects the 3' and 5' hydroxyl groups of two nucleosides through a phosphorous-containing linkage.

In some embodiments, the non-nucleotide linker is a small molecule, macromolecule or biomolecule, including, without limitation, polypeptides, antibodies, lipids, antigens, allergens, and oligosaccharides. In some other embodiments, the non-nucleotide linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens, and antibiotics. However, for purposes of describing the non-nucleotide linker, the term "small molecule" is not intended to include a nucleoside.

In some embodiments, the non-nucleotide linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, triethylene glycol hexaethylene glycol, polyethylene glycol linkers (e.g. [—O—CH2—CH2—]$_n$ (n=1-9)), methyl linkers, ethyl linkers, propyl linkers, butyl linkers or hexyl linkers. In some embodiments, such alkyl linkers may include peptides or amino acids.

In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4.

Some non-nucleotide linkers according to the invention permit attachment of more than two oligonucleotides. For example, the small molecule linker glycerol has three hydroxyl groups to which oligonucleotides may be covalently attached. Some palindromic immune modulatory oligonucleotides according to the invention, therefore, comprise two or more oligonucleotides linked to a nucleotide or a non-nucleotide linker. Such palindromic immune modulatory oligonucleotides are referred to as being "branched".

Palindromic immune modulatory oligonucleotide compounds may comprise at least two oligonucleotides non-covalently linked, such as by electrostatic interactions, hydrophobic interactions, π-stacking interactions, hydrogen bonding and combinations thereof. Non-limiting examples of such non-covalent linkage includes Watson-Crick base pairing, Hoogsteen base pairing and base stacking.

The palindromic immune modulatory oligonucleotides used in this study as exemplar of the invention include, but are not limited to, those depicted in Table 1. The palindromic immune modulatory oligonucleotides contain either identical or non-identical oligonucleotide sequence segments linked or connected through their 3'-ends via a non-nucleoside linker, including but not limited to, glycerol, C3-linker, C3-alkyl linker or propanediol. IMOs 6-9 (SEQ ID NOS 6-9) contain two identical sequence segments, whereas IMOs 1-5 and 10-11 (SEQ ID NOS 1-5, 10-11 and 12-18) contain two unidentical sequence segments. The second palindromic immune modulatory oligonucleotide segment was non-identical and different from the first segment in terms of its length, base composition and/or chemical modifications incorporated.

TABLE 1

Sequences of exemplar palindromic immune modulatory oligonucleotides:

| IMO™ No. | Sequence |
|---|---|
| 1 | 5'-TCG$_1$TCG$_1$TTCTC-Y-G$_1$CTTG$_1$CAAG$_1$CT-5' (SEQ ID NOS 1 and 12) |
| 2 | 5'-TCG$_1$TCG$_1$TTCTC-Y-GAG$_1$CTTG$_1$CAAG$_1$CTCT-5' (SEQ ID NOS 2 and 13) |
| 3 | 5'-TCG$_1$TCG$_1$TTCTC-Y-GAGAG$_1$CTTG$_1$CAAG$_1$CTCTCT-5' (SEQ ID NOS 3 and 14) |
| 4 | 5'-TCG$_1$TCG$_1$TTCTC-Y-GCCGCGCGGC-5' (SEQ ID NOS 4 and 15) |
| 5 | 5'-TCG$_1$TCG$_1$TTAGA-Y-TG$_1$CTG$_1$CT-5' (SEQ ID NOS 5 and 16) |
| 6 | 5'-TCG$_1$AACG$_1$TTCG$_1$-X-G$_1$CTTG$_1$CAAG$_1$CT-5' (SEQ ID NO: 6) |
| 7 | 5'-TCG$_1$TCG$_1$TTCTG-X-GTCTTG$_1$CTG$_1$CT-5' (SEQ ID NO: 7) |
| 8 | 5'-TCTGACG$_1$TTCT-X-TCTTG$_1$CAGTCT-5' (SEQ ID NO: 8) |
| 9 | 5'-ACACACCAACT-X-TCAACCACACA-5' (SEQ ID NO: 9) |
| 10 | 5'-TCG$_1$TCG$_1$TTC-Y-G$_1$CTTG$_1$CAAG$_1$CT-5' (SEQ ID NOS 10 and 17) |
| 11 | 5'-TCG$_2$TCG$_2$TTC-Y-G$_1$CTTG$_1$CAAG$_1$CT-5' (SEQ ID NOS 11 and 18) |

X = Glycerol linker;
Y = C3 linker;
G$_1$ = 7-deaza-dG;
G$_2$ = AraG

As would be recognized by one skilled in the art, the complementary sequence of the palindromic immune modulatory oligonucleotides allows for intermolecular hydrogen bonding thereby giving the palindromic immune modulatory oligonucleotides secondary structure. As used herein, the term "secondary structure" refers to intermolecular hydrogen bonding. Intermolecular hydrogen bonding results in the formation of a double stranded nucleic acid molecule. Additional palindromic immune modulatory oligonucleotides can bind together thereby creating a chain, or multimers, of palindromic immune modulatory oligonucleotides according to the invention.

"Palindromic sequence" shall mean an inverted repeat (i.e., a sequence such as ABCDEE'D'C'B'A' in which A and A', B and B', etc., are bases capable of forming the usual Watson-Crick base pairs. Under appropriate conditions, such as physiological salt and pH conditions, such sequences may form double-stranded structures. In one embodiment the immune modulatory nucleic acid contains a palindromic sequence. A palindromic sequence used in this context refers to a palindrome in which the CpG is part of the palindrome. In some embodiments the CpG is the center of the palindrome.

In some embodiments of this aspect of the invention, the palindromic sequence is self-complementary which, upon suitable alignment, may form intramolecular or, more typically, intermolecular basepairing between G-C, G*-C, G*-C*, G-C*, I-C, A-T, A-U and/or G-U wobble pairs. In one embodiment the extent of self-complementarity is at least 50 percent. For example an 8-mer that is at least 50 percent self-complementary may have a sequence capable of forming 4, 5, 6, 7, or 8 G-C, A-T, A-U and/or G-U wobble basepairs. Such basepairs may but need not necessarily involve bases located at either end of the self-complementary palindromic immune modulatory oligonucleotide. Where nucleic acid stabilization may be important to the palindromic immune modulatory oligonucleotide, it may be advantageous to "clamp" together one or both ends of a double-stranded nucleic acid, either by basepairing or by any other suitable means. The degree of self-complementarity may depend on the alignment between palindromic immune modulatory oligonucleotides, and such alignment may or may not include single- or multiple-nucleoside overhangs. In other embodiments, the degree of self-complementarity is at least 60 percent, at least 70 percent, at least 80 percent, at least 90 percent, or even 100 percent.

Similar considerations apply to intermolecular basepairing between palindromic immune modulatory oligonucleotides of different base sequence. Thus, where a plurality of palindromic immune modulatory oligonucleotides are used together, the plurality of palindromic immune modulatory oligonucleotides may, but need not, include sequences which are at least partially complementary to one another. In one embodiment the plurality of palindromic immune modulatory oligonucleotides includes a palindromic immune modulatory oligonucleotide having a first sequence and a palindromic immune modulatory oligonucleotide having a second sequence, wherein the first sequence and the second sequence are at least 50 percent complementary. For example, as between two 8-mers that are at least 50 percent complementary, they may form 4, 5, 6, 7, or 8 G-C, A-T, A-U, and/or G-U wobble basepairs. Such basepairs may but need not necessarily involve bases located at either end of the complementary palindromic immune modulatory oligonucleotides. The degree of complementarity may depend on the alignment between palindromic immune modulatory oligonucleotides, and such alignment may or may not include single- or multiple-nucleoside overhangs. In other embodiments, the degree of complementarity is at least 60 percent, at least 70 percent, at least 80 percent, at least 90 percent, or even 100 percent.

As used herein, the term "complementary" means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In some embodiments each nucleoside unit includes a heterocyclic base and a pentofuranosyl, 2'-deoxypentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (RP)- or (SP)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids with phosphate groups, locked nucleic acids (LNA), morpholino-backbone oligonucleotides, and oligonucleotides having backbone sections with alkyl linkers or amino linkers.

The palindromic immune modulatory oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethoxyribonucleosides or 2'-O-methoxyethoxyarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One non-limiting example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One non-limiting example of such a hybrid oligonucleotide comprises a ribonucleotide or 2' substituted ribonucleotide region, and a deoxyribonucleotide region (see, e.g., Metelev and Agrawal, U.S. Pat. Nos. 5,652,355, 6,346,614 and 6,143,881).

In a second aspect the invention provides pharmaceutical compositions. These compositions comprise any of the compositions disclosed in the invention and a pharmaceutically acceptable carrier.

As used herein, the term "pharmaceutically acceptable" refers to a material that does not interfere with the effectiveness of the compositions of the first, second or third aspects of the invention and is compatible with a biological system such as a cell, cell culture, tissue, or organism. In certain embodiments, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., Remington's Pharmaceutical Sciences, 18th Edition, ed. A. Gennaro, Mack Publishing Co., Easton, Pa., 1990, ISBN: 0-912734-04-3.

Pharmaceutical compositions of the invention may also include a cancer vaccine, including a cancer vaccine selected from EFG, Anti-idiotypic cancer vaccines, Gp75 antigen, GMK melanoma vaccine, MGV ganglioside conjugate vaccine, Her2/new, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmunCyst/TheraCys.

The palindromic immune modulatory oligonucleotide or the vaccine, or both, may optionally be linked to an immunogenic protein, such as keyhole limpet hemocyanin (KLH), cholera toxin B subunit, or any other immunogenic carrier protein or nonimmunogenic carrier protein. Any of the plethora of adjuvants may be used including, without limitation, Freund's complete adjuvant, Freund's incomplete adjuvant, KLH, monophosphoryl lipid A (MPL), alum, and saponins, including QS-21, imiquimod, R848, or combinations thereof.

In various embodiments of the invention, the compositions of the first or second aspects of the invention may be covalently linked to an antigen or otherwise operatively associated with an antigen. As used herein, the term "operatively associated with" refers to any association that maintains the activity of both the compositions of the first, second or third aspects of the invention and the antigen. Non-limiting examples of such operative associations include being part of the same liposome or other such delivery vehicle or reagent. In embodiments wherein the compositions of the first, second or third aspects of the invention are covalently linked to an antigen, such covalent linkage is at any position on the compositions of the first, second or third aspects of the invention other than an accessible 5' end of a palindromic immune modulatory oligonucleotide. For example, the antigen may be attached at an internucleoside linkage or may be attached to the non-nucleotidic linker. Alternatively, the antigen may itself be the non-nucleotidic linker.

In various embodiments of the invention, the compositions of the first or second aspects of the invention may include a palindromic immune modulatory oligonucleotide with antisense activity. As used herein, "antisense activity" means that the palindromic immune modulatory oligonucleotide, when introduced into a cell or an animal, causes a reduction in the expression of the gene to which it is complementary.

In various embodiments of the invention, the compositions of the first or second aspects of the invention may include a palindromic immune modulatory oligonucleotide sequence that is an aptamer. Aptamers are nucleic acid molecules that have been selected from random pools based on their ability to bind other molecules. Aptamers have been selected which bind nucleic acids, proteins, small organic compounds, and even entire organisms. These novel molecules have many potential uses in medicine and technology (see, e.g., Burgstaller P., et al. *Curr Opin Drug Discov Devel.* 5: 690-700 (2002)).

The pharmaceutical compositions of the invention may be administered by any suitable route, including, without limitation, parenteral, oral, sublingual, transdermal, topical, mucosal, inhalation, intranasal, aerosol, intraocular, intratracheal, intrarectal, vaginal, by gene gun, dermal patch or in eye drop or mouthwash form. The pharmaceutical compositions can be delivered using known procedures at dosages and for periods of time effective obtain the desired effect, e.g. the treatment of cancer, the treatment of infection and the treatment of autoimmune diseases. When administered systemically, the pharmaceutical compositions are administered at a sufficient dosage to attain a blood level of the compositions of the first, second and/or third aspects of the invention from about 0.0001 micromolar to about 10 micromolar. For localized administration, much lower concentrations than this may be effective, and much higher concentrations may be tolerated. In certain embodiments, a total dosage of palindromic immune modulatory oligonucleotide ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

Figure 2:
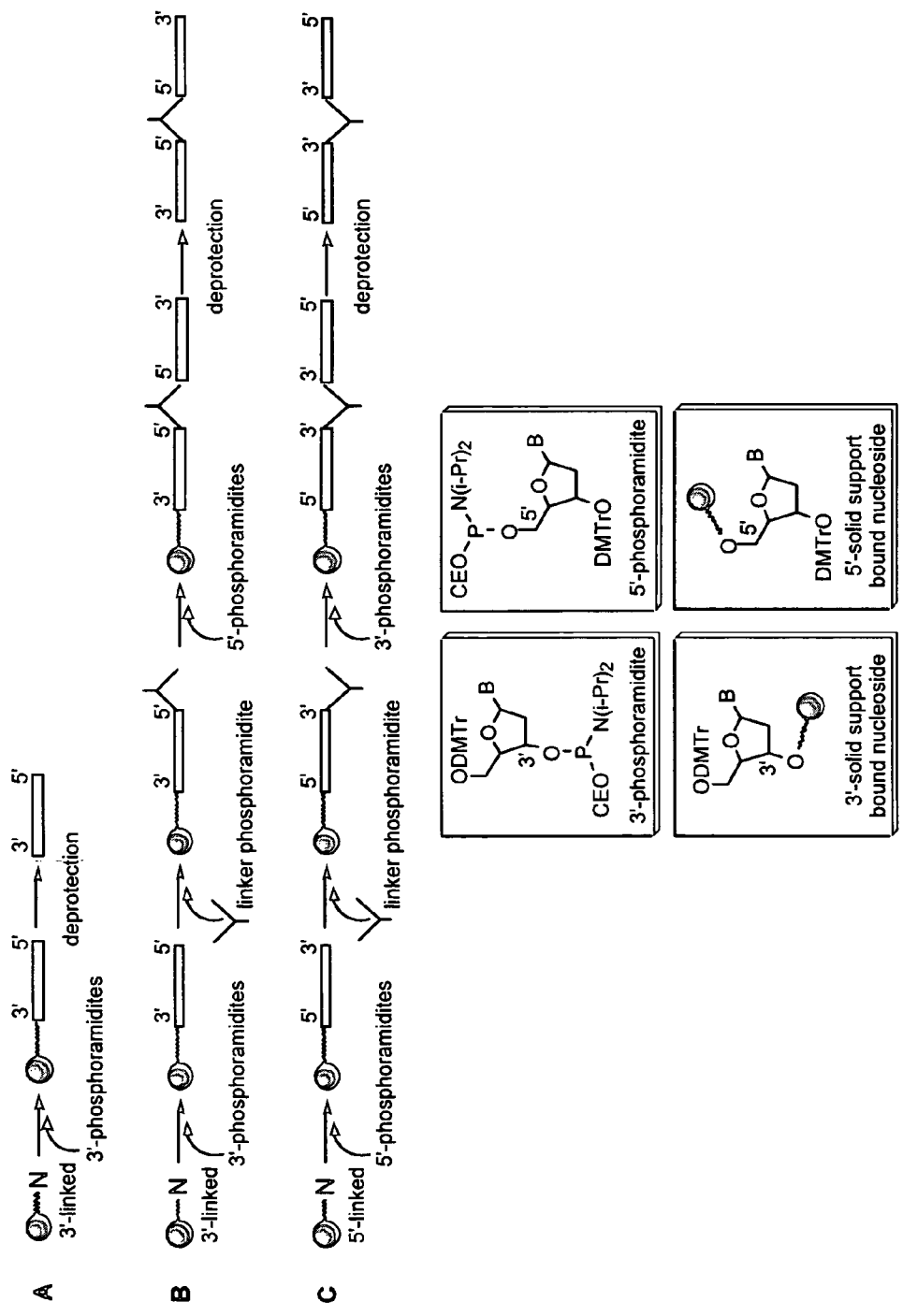
FIG. 2 depicts is a synthetic scheme for the linear synthesis of palindromic immune modulatory oligonucleotides of the invention.

Exemplar palindromic immune modulatory oligonucleotides of the invention were created using the following protocols for synthesis. The palindromic immune modulatory oligonucleotides of the invention may conveniently be synthesized using an automated synthesizer and phosphoramidite approach as schematically depicted in FIG. 2. In some embodiments, the palindromic immune modulatory oligonucleotides are synthesized by a linear synthesis approach. Representative linkers for this synthesis are presented in FIG. 1. As used herein, the term "linear synthesis" refers to a synthesis that starts at one end of the palindromic immune modulatory oligonucleotide and progresses linearly to the other end. Linear synthesis permits incorporation of either identical or un-identical (in terms of length, base composition and/or chemical modifications incorporated) monomeric units into the palindromic immune modulatory oligonucleotides.

At the end of the synthesis, the palindromic immune modulatory oligonucleotides according to the invention may conveniently be deprotected with concentrated ammonia solution or as recommended by the phosphoramidite supplier, if a modified nucleoside is incorporated. The product palindromic immune modulatory oligonucleotides is preferably purified by reversed phase HPLC, detritylated, desalted, and dialyzed.

The compositions disclosed in the first and second aspects of the invention can comprise the palindromic immune modulatory oligonucleotide alone or as palindromic immune modulatory oligonucleotide conjugates. A palindromic immune modulatory oligonucleotide conjugate comprises a palindromic immune modulatory oligonucleotide, as described above, and a compound conjugated to the palindromic immune modulatory oligonucleotide at a position other than the accessible 5' end. In some embodiments, the compound is conjugated to the non-nucleotidic linker. In some other embodiments, the compound is conjugated to the palindromic immune modulatory oligonucleotide at a position other than its 5' end. Suitable compounds which can be conjugated to the palindromic immune modulatory oligonucleotides of the invention include, but are not limited to, cholesterol, different lengths of polyethylene glycol, peptides, antibodies, proteins, vaccines, lipids, antigens and any immune modulatory small molecule such as, but not limited to, imiquimod, R848, loxoribine, isatorbin as well as chemotherapeutic agents. The palindromic immune modulatory oligonucleotide or (see U.S. Patent Publication No. 20040097719) alone or as palindromic immune modulatory oligonucleotide conjugates can be administered in the methods discussed below.

The antigen is optionally selected from antigens associated with a pathogen, antigens associated with a cancer, antigens associated with an auto-immune disorder, and antigens associated with other diseases such as, but not limited to, veterinary or pediatric diseases, or wherein the antigen is an allergen. In some embodiments, the antigen produces a vaccine effect. For purposes of the invention, the term "associated with" means that the antigen is present when the pathogen, cancer, auto-immune disorder, food allergy, skin allergy, respiratory allergy, asthma or other disease is present, but either is not present, or is present in reduced amounts, when the pathogen, cancer, auto-immune disorder, food allergy, skin allergy, respiratory allergy, or disease is absent.

The palindromic immune modulatory oligonucleotide is covalently linked to the antigen, or it is otherwise operatively associated with the antigen. As used herein, the term "operatively associated with" refers to any association that maintains the activity of both palindromic immune modulatory oligonucleotide and antigen. Non-limiting examples of such operative associations include being part of the same liposome or other such delivery vehicle or reagent. In embodiments wherein the palindromic immune modulatory oligonucleotide is covalently linked to the antigen, such covalent linkage preferably is at any position on the palindromic immune modulatory oligonucleotide other than an accessible 5' end of a palindromic immune modulatory oligonucleotide. For example, the antigen may be attached at an internucleoside linkage or may be attached to the non-nucleotidic linker. Alternatively, the antigen may itself be the non-nucleotidic linker.

In a third aspect, the invention provides methods for generating and/or modulating an immune response in a vertebrate, such methods comprising administering to the vertebrate a palindromic immune modulatory oligonucleotide or conjugate according to the invention. In some embodiments, the vertebrate is a mammal. For purposes of this invention, the term "mammal" is expressly intended to include humans. In certain embodiments, the palindromic immune modulatory oligonucleotide or conjugate is administered to a vertebrate in need of immune modulation.

As used herein, the term "modulating" or "modulate" means to increase or decrease the immune modulatory activity of a palindromic immune modulatory nucleic acid relative to that of the parent palindromic immune modulatory nucleic acid.

In the methods according to this aspect of the invention, administration of palindromic immune modulatory oligonucleotides can be by any suitable route, including, without limitation, parenteral, oral, sublingual, transdermal, topical, mucosal, inhalation, intranasal, intramuscular, intraperitonal, subcutaneous, intradermal, aerosol, intraocular, intratracheal, intrarectal, vaginal, by gene gun, dermal patch or in eye drop or mouthwash form. Administration of the therapeutic compositions of immunomers can be carried out using known procedures at dosages and for periods of time effective to reduce symptoms or surrogate markers of the disease. When administered systemically, the therapeutic composition is preferably administered at a sufficient dosage to attain a blood level of palindromic immune modulatory oligonucleotide from about 0.0001 micromolar to about 10 micromolar. For localized administration, much lower concentrations than this may be effective, and much higher concentrations may be tolerated. Preferably, a total dosage of palindromic immune modulatory oligonucleotide ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The methods according to this aspect of the invention are useful for model studies of the immune system. The methods are also useful for the prophylactic or therapeutic treatment of human or animal disease. For example, the methods are useful for pediatric and veterinary vaccine applications.

In a fourth aspect, the invention provides methods for therapeutically treating a vertebrate having a disease or disorder, such methods comprising administering to the vertebrate a palindromic immune modulatory oligonucleotide or conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids, and prions. Administration is carried out as described for the third aspect of the invention.

For purposes of the invention, the term "allergy" includes, without limitation, food allergies atopic dermatitis, allergic rhinitis (also known as hay fever), allergic conjunctivitis, urticaria (also known as hives), respiratory allergies and allergic reactions to other substances such as latex, medications and insect stings or problems commonly resulting from allergic rhinitis-sinusitis, otitis media and COPD. The term "airway inflammation" includes, without limitation, asthma. Specific examples of asthma include, but are not limited to, allergic asthma, non-allergic asthma, exercised-induced asthma, occupational asthma, and nocturnal asthma.

Allergic asthma is characterized by airway obstruction associated with allergies and triggered by substances called allergens. Triggers of allergic asthma include, but are not limited to, airborne pollens, molds, animal dander, house dust mites and cockroach droppings. Non-allergic asthma is caused by viral infections, certain medications or irritants found in the air, which aggravate the nose and airways. Triggers of non-allergic asthma include, but are not limited to, airborne particles (e.g., coal, chalk dust), air pollutants (e.g., tobacco smoke, wood smoke), strong odors or sprays (e.g., perfumes, household cleaners, cooking fumes, paints or varnishes), viral infections (e.g., colds, viral pneumonia, sinusitis, nasal polyps), aspirin-sensitivity, and gastroesophageal reflux disease (GERD). Exercise-induced asthma (EIA) is triggered by vigorous physical activity. Symptoms of EIA occur to varying degrees in a majority of asthma sufferers and are likely to be triggered as a result of breathing cold, dry air while exercising. Triggers of EIA include, but are not limited to, breathing airborne pollens during exercise, breathing air pollutants during exercise, exercising with viral respiratory tract infections and exercising in cold, dry air. Occupational asthma is directly related to inhaling irritants and other potentially harmful substances found in the workplace. Triggers of occupational asthma include, but are not limited to, fumes, chemicals, gases, resins, metals, dusts, vapors and insecticides.

As used herein, the term "autoimmune disorder" refers to disorders in which "self" proteins undergo attack by the immune system. Such term includes autoimmune asthma.

In a fifth aspect the invention provides a method for preventing cancer, an autoimmune disorder, airway inflammation, inflammatory disorders, skin disorders, allergy, asthma or a disease caused by a pathogen in a vertebrate. This method comprises administering to the vertebrate any of the compositions, alone or in combination, disclosed in the invention. Pathogens include bacteria, parasites, fungi, viruses, viroids and prions. Administration is carried out as described for the third aspect of the invention.

In any of the methods according to the invention, the palindromic immune modulatory oligonucleotide or a conjugate thereof can be administered in combination with any other agent useful for treating the disease or condition that does not diminish the immune modulatory effect of the palindromic immune modulatory oligonucleotide. For purposes of this aspect of the invention, the term "in combination with" means in the course of treating the same disease in the same patient, and includes administering the palindromic immune modulatory oligonucleotide and an agent in any order, including simultaneous administration, as well as any temporally spaced order, for example, from sequentially with one immediately following the other to up to several days apart. Such combination treatment may also include more than a single administration of the palindromic immune modulatory oligonucleotide, and independently the agent. The administration of the palindromic immune modulatory oligonucleotide and agent may be by the same or different routes.

In any of the methods according to the invention, the palindromic immune modulatory oligonucleotide or palindromic immune modulatory oligonucleotide conjugate can be administered in combination with any other agent useful for treating or preventing the disease or condition that does not diminish the immune stimulatory effect of the palindromic immune modulatory oligonucleotide. In any of the methods according to the invention, the agent useful for treating the disease or condition includes, but is not limited to, vaccines, antigens, antibodies, cytotoxic agents, allergens, antibiotics, antisense oligonucleotides, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides and peptides comprising modified amino acids. For example, in the treatment of cancer, it is contemplated that the palindromic immune modulatory oligonucleotide or palindromic immune modulatory oligonucleotide conjugate may be administered in combination with a chemotherapeutic compound or a monoclonal antibody. Alternatively, the agent can include DNA vectors encoding for antigen or allergen. In these embodiments, the palindromic immune modulatory oligonucleotides of the invention can variously act as adjuvants and/or produce direct immune modulatory effects.

Preferred chemotherapeutic agents used in the method according to the invention include, without limitation Gemcitabine, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26), Vindesine sulfate, tyrosine kinase inhibitors, such as EGFR and VEGF inhibitors including, but not limited to, Lapatinib (EGFR and ErbB-2 (Her2/neu) dual tyrosine kinase inhibitor (GSK)), Gefitinib (ZD1839/Iressa (AstraZeneca)), Erlotinib (Tarceva—EGFR/HER1 inhibitor (Genentech)), Thalidomide ((Thalidomide)—anti-angeogenic drug), Imatinib (Glivec) and Vatalanib (VEGFR tyrosine kinase inhibitor), Sorafenib (Raf kinase inhibitor (Bayer)), VX-680 (Aurora kinase inhibitor), Sutent (Receptor Tyrosine Kinases (RTKs) inhibitor (Pfizer)), Bortezomib ((Velcade) proteosome inhibitor), Temozolomide ((Temodal) alkylating agent), and Interferon alpha (Intron A, Roferon A).

Passive immunotherapy in the form of antibodies, and particularly monoclonal antibodies, has been the subject of considerable research and development as anti-cancer agents. The term "monoclonal antibody" as used herein refers to an antibody molecule of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. Examples of anti-cancer agents include, but are not limited to, Panorex (Glaxo-Welicome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech), Herceptin (Genentech/Hoffinan la Roche), Cetuximab (Imclone) and Panitumumab (Abgenix/Amgen). Antibodies may also be employed in active immunotherapy utilizing anti-idiotype antibodies which appear to mimic (in an immunological sense) cancer antigens. Monoclonal antibodies can be generated by methods known to those skilled in the art of recombinant DNA technology.

The examples below are intended to further illustrate certain preferred embodiments of the invention, and are not intended to limit the scope of the invention.

EXAMPLES

Example 1

Synthesis and Purification of phosphorotioate CpR palindromic Immune Modulatory oligonucleotides with Unidentical Sequence Segments Palindromic immune modulatory oligonucleotides were synthesized on a 1-2 μmol scale using β-cyanoethylphosphoramidite chemistry on a PerSeptive Biosystem's 8909 Expedite DNA synthesizer. Di-DMT protected glyceryl linker attached to CPG solid-support and DMT-propanediol phosphoramidite linker were obtained from ChemGenes Corporation (Wilmington, Mass.). 5'-CPG loaded T monomer, 5'-phosphoramidites and 7-deaza-2'-deoxyguanosine 3'-phosphramidite were obtained from ChemGenes. The 3'-phosphoramidites of dA, dG, dC and T were obtained from Proligo. Beaucage reagent was used as an oxidant to obtain the phosphorothioate backbone modification. A modified coupling protocol was used for 5'-phosphoramidites and 7-deaza-2'-deoxyguanosine 3'-phosphoramidites. After the synthesis, immunomers were deprotected using standard protocols, purified by RP-HPLC, detritylated and dialyzed against United States Pharmacopea quality sterile water for irrigation (Braun). The palindromic immune modulatory oligonucleotides were lyophilized and dissolved again in distilled water and the concentrations were determined by measuring the UV absorbance at 260 nm. The purity of all the palindromic immune modulatory oligonucleotides synthesized was determined by denaturing PAGE and some of the palindromic immune modulatory oligonucleotides were characterized by MALDI-TOF mass spectrometry for molecular mass. All palindromic immune modulatory oligonucleotides were synthesized and purified under identical conditions to minimize endotoxin contamination.

Example 2

Mouse Spleen Cell Cultures and Cytokine Measurement

Figure 3:
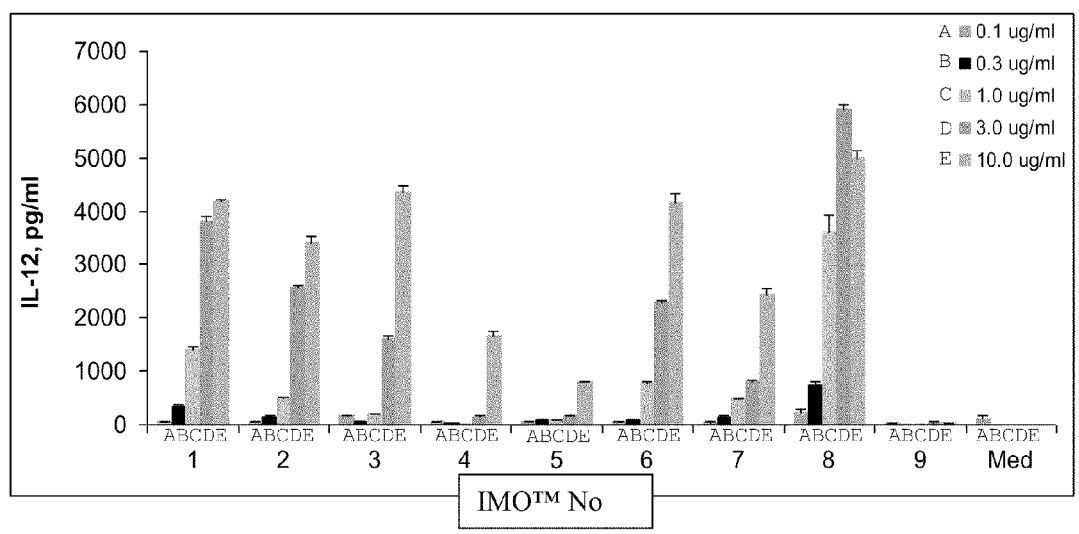
FIG. 3 depicts IL-12 induction in C57BL/6 mouse spleen cell cultures by exemplar palindromic immune modulatory oligonucleotides according to the invention. More generally, FIG. 3 demonstrates that varying the length, base composition and/or chemical modifications of the palindromic immune modulatory oligonucleotide will generate distinct IL-12 induction and that unique IL-12 induction is generated at each concentration for each palindromic immune modulatory oligonucleotide. C57BL/6 mouse spleen cells were treated with oligonucleotides corresponding to the indicated SEQ ID NO at the indicated does. Med=control/media treatment group.
Figure 4:
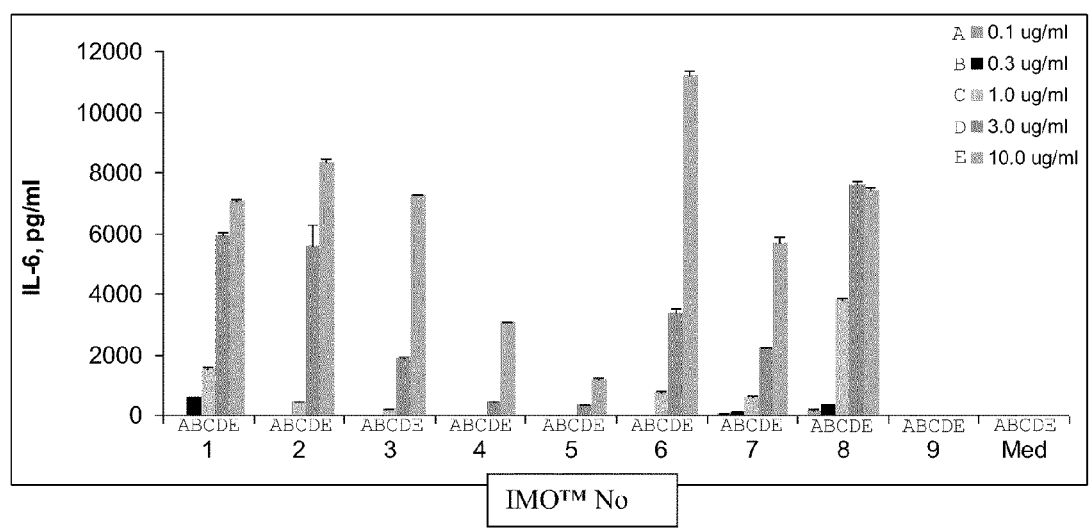
FIG. 4 depicts IL-6 induction in C57BL/6 mouse spleen cell cultures by exemplar palindromic immune modulatory oligonucleotides according to the invention. More generally, FIG. 4 demonstrates that varying the length, base composition and/or chemical modifications of the palindromic immune modulatory oligonucleotide will generate a distinct IL-6 induction and that unique IL-6 induction is generated at each concentration for each palindromic immune modulatory oligonucleotide. C57BL/6 mouse spleen cells were treated with oligonucleotides corresponding to the indicated SEQ ID NO at the indicated does. Med=control/media treatment group.
Figure 5:
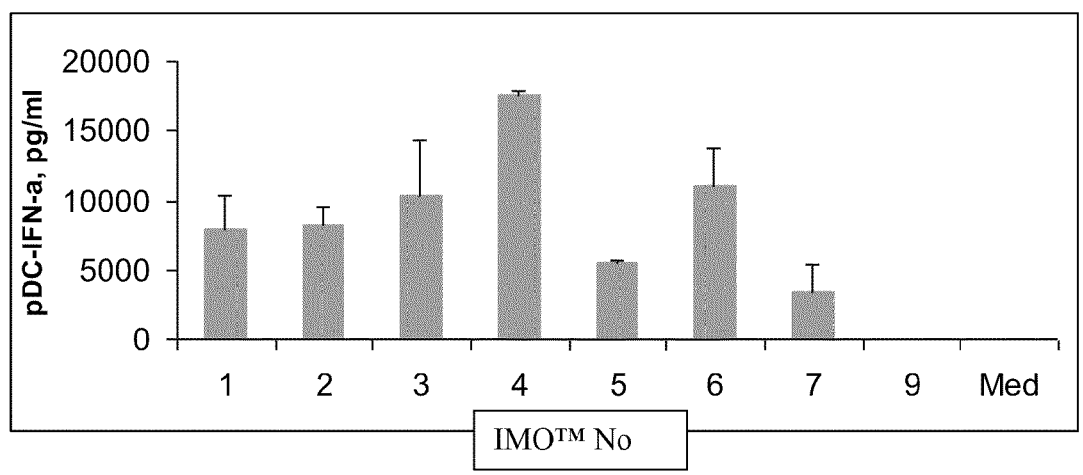
FIG. 5 depicts IFN-α induction in human pDC cultures by exemplar palindromic immunomodulatory oligonucleotides according to the invention. More generally, FIG. 5 demonstrates that varying the length, base composition and/or chemical modifications of the palindromic immune modulatory oligonucleotide will generate a distinct IFN-α induction. Human pDCs were treated with oligonucleotides corresponding to the indicated SEQ ID NO at 10 μg/mL. Med=control/media treatment group.
Figure 6:
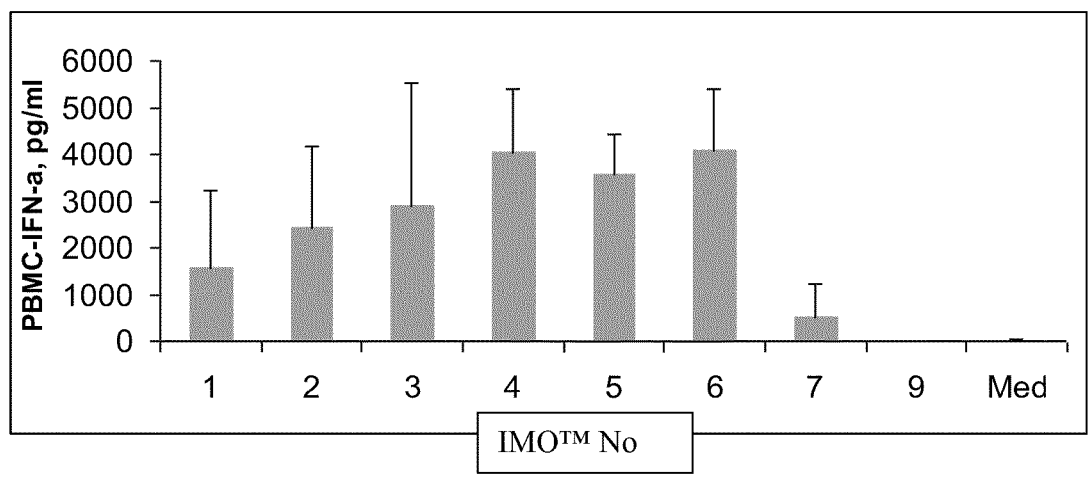
FIG. 6 depicts IFN-α induction in human PBMC cultures by exemplar palindromic immune modulatory oligonucleotides according to the invention. More generally, FIG. 6 demonstrates that varying the length, base composition and/or chemical modifications of the palindromic immune modulatory oligonucleotide will generate a distinct IFN-α induction. Human PBMCs were treated with oligonucleotides corresponding to the indicated SEQ ID NO at 10 μg/mL. Med=control/media treatment group.
Figure 7:
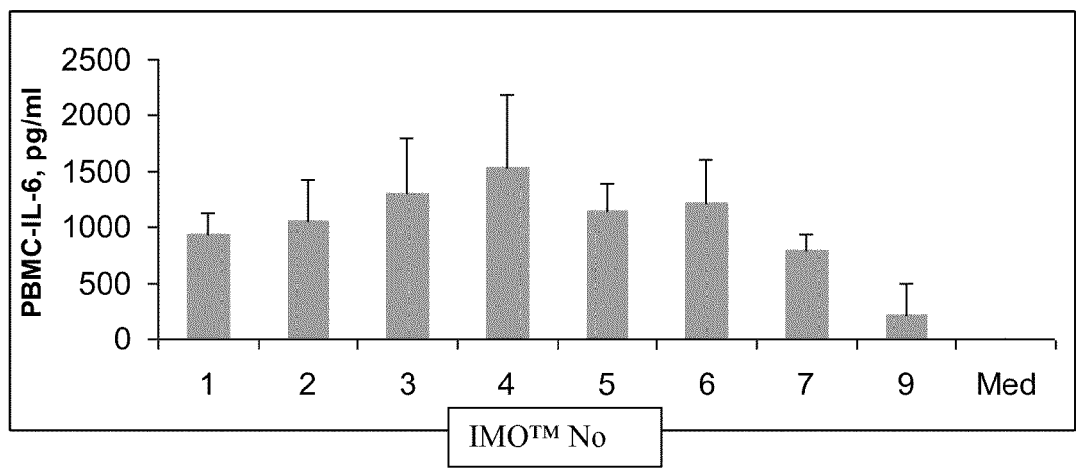
FIG. 7 depicts IL-6 induction in human PBMC cultures by exemplar palindromic immune modulatory oligonucleotides according to the invention. More generally, FIG. 7 demonstrates that varying the length, base composition and/or chemical modifications of the palindromic immune modulatory oligonucleotide will generate a distinct IL-6 induction. Human PBMCs were treated with oligonucleotides corresponding to the indicated SEQ ID NO at 10 μg/mL. Med=control/media treatment group.
Figure 8:
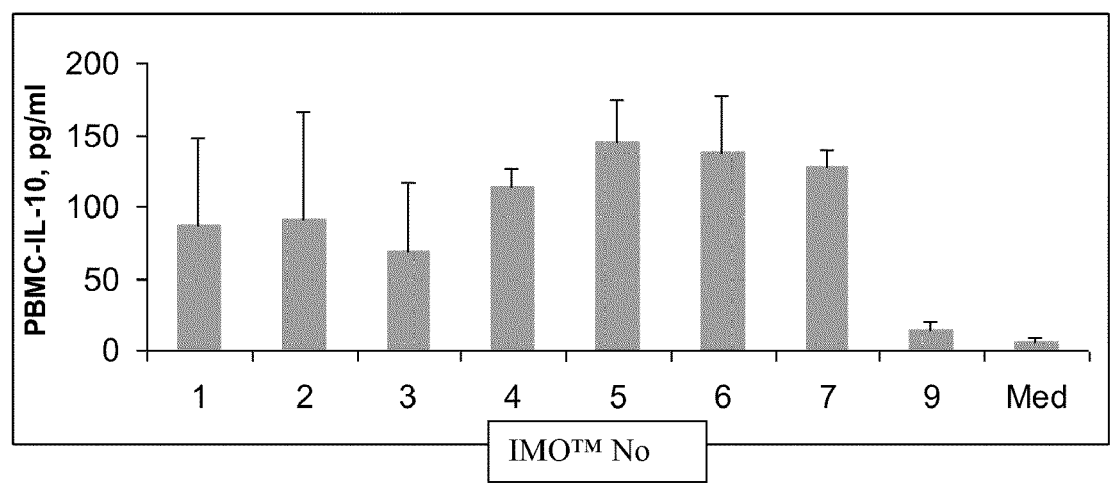
FIG. 8 depicts IL-10 induction in human PBMC cultures by exemplar palindromic immune modulatory oligonucleotides according to the invention. More generally, FIG. 8 demonstrates that varying the length, base composition and/or chemical modifications of the palindromic immune modulatory oligonucleotide will generate a distinct IL-6 induction. Human PBMCs were treated with oligonucleotides corresponding to the indicated SEQ ID NO at 10 μg/mL. Med=control/media treatment group.
Figure 9:
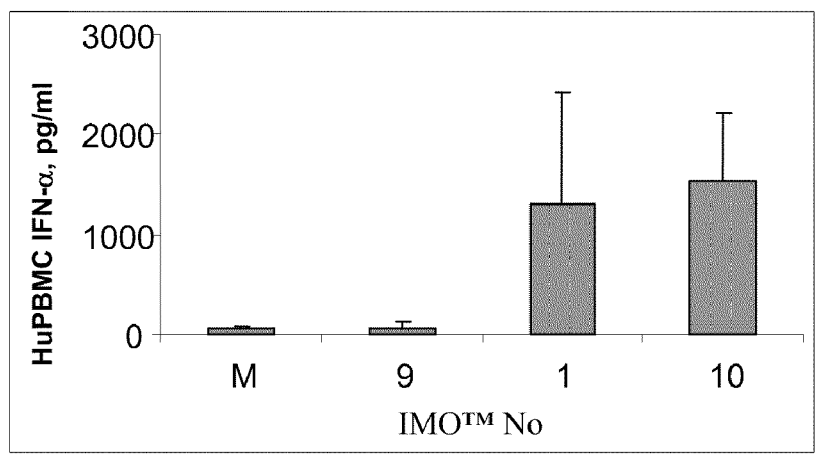
FIG. 9(a) depicts IFN-α induction in human PBMC cultures by exemplar palindromic immune modulatory oligonucleotides according to the invention. More generally, FIG. 9(a) demonstrates that varying the length, base composition and/or chemical modifications of the palindromic immune modulatory oligonucleotide will generate a distinct IFN-α induction. Human PBMCs were treated with oligonucleotides corresponding to the indicated SEQ ID NO at 10 μg/mL. Med=control/media treatment group.
FIG. 9(b) depicts IL-6 induction in human PBMC cultures by exemplar palindromic immune modulatory oligonucleotides according to the invention. More generally, FIG. 9(b) demonstrates that varying the length, base composition and/or chemical modifications of the palindromic immune modulatory oligonucleotide will generate a distinct IL-6 induction. Human PBMCs were treated with oligonucleotides corresponding to the indicated SEQ ID NO at 10 μg/mL. Med=control/media treatment group.
FIG. 9(c) depicts IFN-α induction in human pDC cultures by exemplar palindromic immune modulatory oligonucleotides according to the invention. More generally, FIG. 9(c) demonstrates that varying the length, base composition and/or chemical modifications of the palindromic immune modulatory oligonucleotide will generate a distinct IFN-α induction. Human PBMCs were treated with oligonucleotides corresponding to the indicated SEQ ID NO at 10 μg/mL. Med=control/media treatment group.
Figure 9:
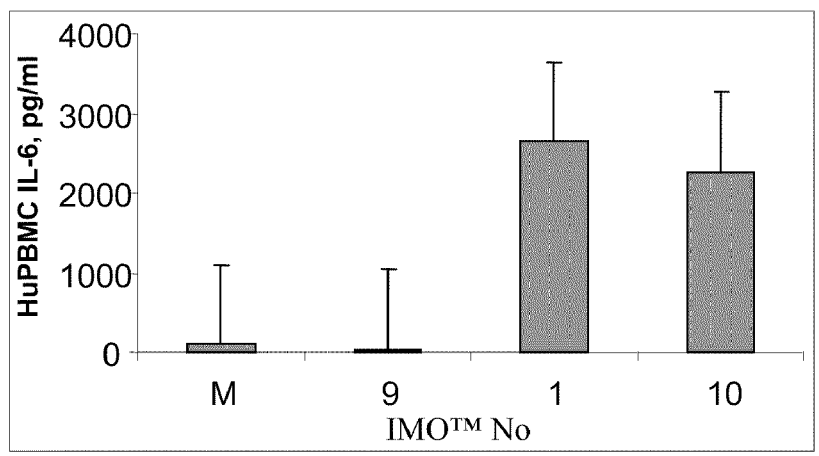
Figure 9:
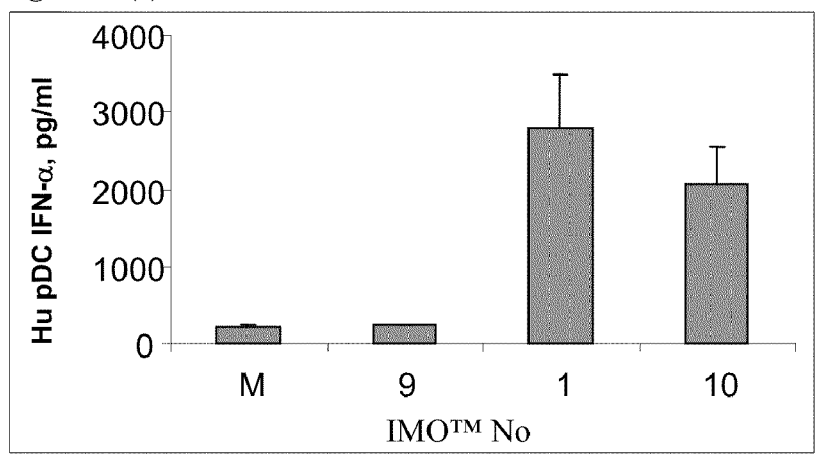

Spleen cells from 4-8 week old C57BL/6 mice were prepared and cultured in RPMI complete medium. Mouse spleen cells were plated in 24-well dishes at $5 \times 10^6$ cells/ml. Palindromic immune modulatory oligonucleotides dissolved in TE buffer (10 mM Tris-HCL, pH 7.5, 1 mM EDTA) were added to a final concentration of 0.1, 0.3, 1.0, 3.0 or 10 μg/ml to the cell cultures. The cells were then incubated at 37° C. for 24 hr and the supernatants were collected for ELISA assays. IL-12 and IL-6 levels in supernatants were measured by sandwich ELISA. The required reagents including cytokine antibodies and standards were purchased from BD Pharmingen. Streptavidin-Peroxidase and substrate were obtained from KPL. The results are shown in FIGS. 3 and 4.

Example 3

Human Cell Cultures and Cytokine Assays

Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma). Plasmacytoid DCs were isolated from PBMCs by positive selection using the BDCA4 cell isolation kits (Miltenyi Biotec) according to the manufacturer's instructions. Human PBMCs were plated in 48-well plates using $5 \times 10^6$ cells/ml. pDCs were plated in 96-well dishes using $1 \times 10^6$ cells/ml. The palindromic immune modulatory oligonucleotides dissolved in DPBS (pH 7.4; Mediatech) were added to a final concentration of 10.0 μg/ml to the cell cultures. The cells were then incubated at 37° C. for 24 hr (IFN-α and IL-6) or 48 hr (IL-10) and the supernatants were collected for ELISA assays. The experiments were performed in triplicate wells. The levels of IFN-α, IL-6 and/or IL-were measured by sandwich ELISA. The required reagents, including cytokine antibodies and standards, were purchased from BD PharMingen. The results are shown in FIGS. 5 through 9.

Equivalents

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. An immune modulatory oligonucleotide having a structure selected from 5'-TCG$_i$TCG$_i$TTCTC-Y-G$_i$CTTG$_i$-CAAG$_i$CT-5' (SEQ ID NO: 1), wherein X is a glycerol linker, Y is C3-linker and Gl is 7-deazaguanosine.

2. A pharmaceutical formulation comprising the immune modulatory oligonucleotide according to claim 1 and a physiologically acceptable carrier.

3. A method for generating an immune response in a vertebrate, the method comprising administering to the vertebrate an palindromic immune modulatory oligonucleotide having a structure selected from 5'-TCG$_i$TCG$_i$TTCTC-Y-G$_i$CTTG$_i$CAAG$_i$CT-5' (SEQ ID NO: 1), wherein X is a glycerol linker, Y is C3-linker and Gl is 7-deazaguanosine.

4. The method according to claim 3, wherein the route of administration is selected from parenteral, oral, sublingual, transdermal, topical, mucosal, inhalation, intranasal, aerosol, intraocular, intratracheal, intrarectal, vaginal, gene gun, dermal patch, eye drop and mouthwash.

5. The pharmaceutical composition according to claim 2 further comprising an antibody, antisense oligonucleotide, protein, antigen, chemotherapeutic agent or adjuvant.

6. The method according to claim 3, further comprising administering an antibody, antisense oligonucleotide, protein, antigen, chemotherapeutic agent or adjuvant.

7. The pharmaceutical composition according to claim 5, wherein the antigen is an allergen.

8. The method according to claim 6, wherein the antigen is an allergen.

* * * * *

UNITED STATES PATENT AND TRADEMARK OFFICE
CERTIFICATE OF CORRECTION

PATENT NO. : 7,786,089 B2
APPLICATION NO. : 11/641551
DATED : August 31, 2010
INVENTOR(S) : Ekambar R. Kandimalla, Mallikarjuna Reddy Putta and Sudhir Agrawal It is certified that error appears in the above-identified patent and that said Letters Patent is hereby corrected as shown below:

The printed claims are replaced by the following claims, based on the amendment entered on April 15, 2010, which was not reflected in the printed claims.

Col. 27 and 28

1. An immune modulatory oligonucleotide having a structure selected from
5'-TCG1TCG1TTCTC-Y-G1CTTG1CAAG1CT-5',
5'-TCG1TCG1TTCTC-Y-GAG1CTTG1CAAG1CTCT-5',
5'-TCG1TCG1TTCTC-Y-GAGAG1CTTG1CAAG1CTCTCT-5',
5'-TCG1TCG1TTCTC-Y-GCCGCGCGGC-5',
5'-TCG1TCG1TTAGA-Y-TG1CTG1CT-5', or 5'-TCG1TCG1TTC-Y-G1CTTG1CAAG1CT-5';
wherein X is a glycerol linker, Y is C3-linker and G1 is 7-deazaguanosine.
2. A pharmaceutical formulation comprising the immune modulatory oligonucleotide according to claim 1 and a physiologically acceptable carrier.
3. A method for generating an immune response in a vertebrate, the method comprising administering to the vertebrate an immune modulatory oligonucleotide having a structure selected from
5'-TCG1TCG1TTCTC-Y-G1CTTG1CAAG1CT-5',
5'-TCG1TCG1TTCTC-Y-GAG1CTTG1CAAG1CTCT-5',
5'-TCG1TCG1TTCTC-Y-GAGAG1CTTG1CAAG1CTCTCT-5',
5'-TCG1TCG1TTCTC-Y-GCCGCGCGGC-5', 5'-TCG1TCG1TTAGA-Y-TG1CTG1CT-5', or
5'-TCG1TCG1TTC-Y-G1CTTG1CAAG1CT-5'; wherein X is a glycerol linker, Y is C3-linker and G1 is 7-deazaguanosine.
4. The method according to claim 3, wherein the route of administration is selected from parenteral, oral, sublingual, transdermal, topical, mucosal, inhalation, intranasal, aerosol, intraocular, intratracheal, intrarectal, vaginal, gene gun, dermal patch, eye drop and mouthwash.
5. The pharmaceutical composition according to claim 2 further comprising an antibody, antisense oligonucleotide, protein, antigen, chemotherapeutic agent or adjuvant.
6. The method according to claim 3, further comprising administering an antibody, antisense oligonucleotide, protein, antigen, chemotherapeutic agent or adjuvant.

Signed and Sealed this
Twenty-eighth Day of December, 2010

David J. Kappos
*Director of the United States Patent and Trademark Office*

7. The pharmaceutical composition according to claim 5, wherein the antigen is an allergen.

8. The method according to claim 6, wherein the antigen is an allergen.